United States Patent [19]

Baker et al.

[11] 4,288,605
[45] Sep. 8, 1981

[54] CYCLOHEXANE CARBONYLOXYBROMOACETANILIDE

[75] Inventors: Don R. Baker, Orinda; Eugene G. Teach, El Cerrito, both of Calif.

[73] Assignee: Stauffer Chemical Company, Westport, Conn.

[21] Appl. No.: 112,252

[22] Filed: Jan. 15, 1980

Related U.S. Application Data

[60] Continuation of Ser. No. 960,378, Nov. 13, 1978, abandoned, which is a division of Ser. No. 560,843, Mar. 21, 1975, abandoned, which is a division of Ser. No. 311,034, Nov. 30, 1972, Pat. No. 3,898,273, which is a continuation-in-part of Ser. No. 127,760, Mar. 24, 1971, abandoned, which is a division of Ser. No. 806,717, Mar. 12, 1969, abandoned.

[51] Int. Cl.$^3$ .................... C07C 69/75; A01N 37/08
[52] U.S. Cl. .................... 560/1; 260/456 A;
260/463; 260/465 D; 424/298; 424/300; 424/301; 424/304; 424/305; 424/308; 424/311; 424/320; 424/324; 546/245; 560/33; 560/136; 560/142; 564/214
[58] Field of Search .................... 560/64, 65, 72, 73, 560/136, 1; 260/465 A, 562 B

[56] References Cited

U.S. PATENT DOCUMENTS

| | | | |
|---|---|---|---|
| 3,032,555 | 5/1962 | Oxley et al. | 260/268 |
| 3,592,949 | 7/1971 | Teach et al. | 560/136 |
| 3,836,564 | 9/1974 | Bauer et al. | 260/456 A |
| 3,898,273 | 8/1975 | Bauer et al. | 560/136 X |

FOREIGN PATENT DOCUMENTS

855556  12/1960  United Kingdom ................. 560/64

OTHER PUBLICATIONS

Jacobs et al., Chemical Abstracts, vol. 9, 2072 to 2074 (1915).
Smirnov (I), Chemical Abstracts, vol. 49, #5357 (1955).
Smirnov (II), Chemical Abstracts, vol. 52, 7199 to 7200 (1957).

*Primary Examiner*—Floyd D. Higel
*Attorney, Agent, or Firm*—Harry A. Pacini

[57] ABSTRACT

Esterified bromoacetanilides as new compositions of matter useful as microbiocides, especially 3'-cyclohexane carbonyloxybromoacetanilide.

1 Claim, No Drawings

CYCLOHEXANE CARBONYLOXYBROMOACETANILIDE

This is a continuation of Application Ser. No. 960,378 filed Nov. 13, 1978, now abandoned, which in turn was a divisional application of then co-pending U.S. Ser. No. 560,843 filed Mar. 21, 1975, now abandoned, which in turn was a divisional application of U.S. Ser. No. 311,034 filed Nov. 30, 1972, now U.S. Pat. No. 3,898,273 issued Aug. 5, 1975, which in turn was a continuation-in-part application of then co-pending U.S. Ser. No. 127,760 filed Mar. 24, 1971, now abandoned, which in turn was a divisional application of then co-pending U.S. Ser. No. 806,717 filed Mar. 12, 1969, now abandoned.

This invention relates to certain new organic compounds which are useful as effective biostatic agents. More specifically, this invention relates to certain bromoacetanilides and their utility in bacteriostatic and fungistatic compositions.

The compounds of the instant invention correspond to the general formula

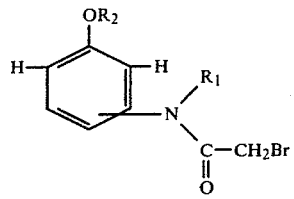

wherein $R_1$ is hydrogen or lower alkyl having from 1 to about 4 carbon atoms, inclusive, $R_2$ represents (1) hydrogen;

(2)

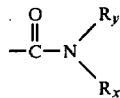

in which $R_x$ and $R_y$ are independently hydrogen, alkyl, allyl, lower alkoxyalkyl, cyclohexyl, 2-chloroallyl, phenyl, benzyl, or substituted-phenyl in which the substituents are chloro, nitro, lower alkyl, lower alkoxy or cyano, $R_x$ and $R_y$ taken together represents an alkylene containing 4 to 6 carbon atoms, inclusive, or lower alkyl-substituted alkylene containing a total of 5 to 8 carbon atoms, inclusive;

(3)

in which $R_A$ is alkyl, phenyl, substituted-phenyl in which the substituents are chloro, nitro, lower alkyl, lower alkoxy or cyano;

(4)

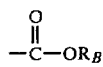

in which $R_B$ is alkyl, phenyl, substituted-phenyl in which the substituents are chloro, nitro, lower alkyl, lower alkoxy or cyano;

(5)

in this $R_C$ is hydrogen, alkyl, cyclohexyl, haloalkyl, phenyl, substituted phenyl in which the substituents are chloro, nitro, lower alkyl, lower alkoxy or cyano; provided that when $R_2$ hydrogen and $R_1$ is hydrogen, then the group

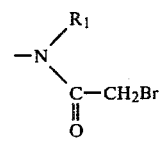

is substituted in the meta-position; and provided that when $R_2$ is

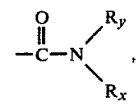

then the group

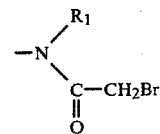

is in the meta-position. The above compounds as well as compounds in which $R_2$ is hydrogen and $R_1$ is hydrogen and

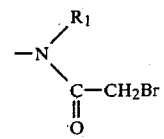

is in the para-position, are effective microbiocides.

In the above description, the following preferred embodiments are intended for the various groups. Alkyl preferably includes, unless otherwise provided for, those members which contain from 1 to about 6 carbon atoms, inclusive, in both straight chain and branched chain configurations, for example, methyl, ethyl, n-propyl, isopropyl, n-butyl, sec.-butyl, amyl, isoamyl, n-hexyl, isohexyl, and the like; and lower alkoxyalkyl preferably includes those members which contain a total of not more than 6 carbon atoms, for example, methoxymethyl, methoxyethyl, ethoxymethyl, methoxypropyl, ethoxypropyl, propoxypropyl, ethoxybutyl, methoxyamyl, and the like. Haloalkyl preferably includes those alkyl members which contain from 1 to about 4 carbon atoms, inclusive, and are substituted with at least one halogen such as chlorine, bromine and iodine. Lower alkyl and lower alkoxy preferably include those members which contain from 1 to about 4 carbon atoms, inclusive, in either straight chain or branched chain configurations.

The compounds herein described can be prepared by one of several methods, depending upon the nature of the starting materials and products desired. The compound 3'-hydroxybromoacetanilide within the scope of this invention can be conveniently prepared by the condensation of m-aminophenol and bromoacetyl bromide. This preparation is specifically described in Example I below. Starting with either the 3'- or 4'- hydroxybromoacetanilide, subsequent condensation reactions can be performed which will ultimately yield other members of this series. Generally, these reactions are performed in a suitable solvent, such as benzene, toluene, acetone, methylethyl ketone and the like. The monosubstituted carbamate condensation reactions are carried out employing the appropriate isocyanate in the presence of catalysts, such as triethylene diamine and dibutyltin dilaurate, in order to facilitate the completion of the reaction. Alternatively, the carbamate derivatives disclosed herein, preferably when $R_x$ and $R_y$ are both hydrogen, are prepared by conversion of the substituted-phenol to the corresponding chloroformate using phosgene, followed by reaction with the appropriate primary or secondary amine or ammonia. The preparation of the sulfonate, dialkyl carbamate, carbonate and carboxylate derivatives are prepared using the appropriate acid halide and an acid acceptor such as pyridine, triethylamine, sodium bicarbonate and the like. After the reaction is completed, the solvent is removed and the product recovered therefrom. Upon isolation of the crude product, final recovery of the purified material is accomplished by normal workup procedures, such as crystallization or distillation.

It has been found that the compounds as defined supra are effective bacteriostatic and fungistatic agents. Whereas microbiological growths on various substances cause deterioration by the presence of the infestation, the application of an agent to retard this adverse growth is desired. Such substances liable to fungus and bacterial infection include cloth, leather, paint, soaps, paper, wood, plastic, oil, and the like. It is contemplated herein that the microbiocidal compositions of the present invention may be effectively incorporated or applied to any of the substances susceptible to microbiological growths.

For maximum effectiveness, the active ingredients of the present invention are admixed in microbiostatically effective amounts with an inert adjuvant. In order to provide formulations particularly adapted for ready and efficient application to the materials to be treated, such formulations comprise those of both the liquid and solid types as well as the "aerosol" type formulations. Application can be directly to the substance to be protected from fungus and bacterial growth. In the pure state, the active ingredient may be too effective or too potent in some applications to have practical utility. A convenient method of treating cloth is by formulating the active ingredient with a soap or detergent and thereby imparting antiseptic or microbiocidal properties to the cloth as it is washed therewith.

For most effective protection it is preferred to apply the materials in intimate contact but thoroughly dispersed on or nearly in the surface to be protected. Therefore, the active ingredients have incorporated therewith a relatively inert agent or adjuvant as a dispersing medium, utilizing methods well known to those skilled in the art.

Suitable formulations of the compounds of this invention comprise the above-defined active ingredients and a suitable material as an adjuvant therefor. Fungistat and bacteriostat compositions are advantageously formulated by first preparing a solution thereof in an organic solvent and then adding the resulting solution to water or other carier. If necessary, an emulsifying agent may be employed. The compositions may also be incorporated into solid carriers such as clay, talc, pumice, soap, and the like. They may also be dissolved in liquefied gases such as fluorochloroethanes or methyl chloride and applied from aerosol bombs containing the solution. It should be noted that suitable formulations may also include adhesive agents, indicators, and other microbiocidal ingredients. Other ingredients may be supplementary insecticides, fungicides, bacteriocides, nematocides or selective herbicides.

Since the amount of active agent of the present invention which is employed will vary with the microbiocidal effect sought, the utility of the treated material, type and dimensions of the material treated, it is evident that no rigid limits can be set forth on the quantity required. Determination of the optimum effective concentration for a specific performance is readily ascertainable by routine procedures, as will be apparent to those skilled in the art.

Preparation of the compounds of the present invention are illustrated by the following particular examples. Following the examples is a table of compounds which are prepared according to the procedures described herein.

EXAMPLE I

Preparation of 3'-hydroxybromoacetanilide m-Aminophenol, 66.5 g. (0.61 mole), is dissolved in 500 ml. of a 50/50 (v/v) mixture of glacial acetic acid and saturated sodium acetate solution. The mixture is cooled to approximately 10° C. and 200 g. (0.99 mole) of bromoacetyl bromide is added dropwise. The temperature is maintained between 15° and 20° C. When addition is complete, the mixture is stirred while cooling until the temperature is about 5° C. The product is filtered off, washed successively with cold water, saturated sodium bicarbonate solution and finally two portions of water. The product is dried under vacuum. The yield of the title compound is 121 g. (86 percent of theory), m.p. 167°–170° C.

EXAMPLE II

Preparation of 3'-N-methyl carbamoyloxy bromoacetanilide 3-hydroxybromoacetanilide, 34.5 g. (0.15 mole) in 250 ml. of acetone containing approximately 100 mg. of triethylene diamine and 5 drops of dibutyltin dilaurate is refluxed for two hours with 9.4 g. (0.165 mole) of methyl isocyanate. On cooling, the product crystallizes from solution and is recovered by filtration. There is obtained 24 g. (56 percent of theory) of the title compound. m.p. 136°–138° C.

EXAMPLE III

Preparation of 3'-propionoxy bromoacetanilide

The anilide, 3'-hydroxy bromoacetanilide, 6.9 g. and propionyl chloride (3.1 g., 0.033 mole) are combined in 120 ml. of methylene chloride as a solvent. Pyridine (2.6 g., 0.033 mole) is added dropwise. A slightly exothermic reaction takes place during the addition. Stirring is continued at room temperature for 20 minutes. A clear solution is obtained. The material is washed sucessively with water, dilute hydrochloric acid and again with water. The organic layer is dried over anhydrous magnesium sulfate and the solvent evaporated. The resulting material is recrystallized from a mixture of ethylacetate and ether. There is obtained 6.5 g. of the title compound, m.p. 85°–88° C.

EXAMPLE IV

Preparation of 3'-bromoacetoxy bromoacetanilide

Meta-aminophenol, 5.5 g., 0.05 mole, is held in suspension in 200 ml. methylene chloride solvent. To this solution is added 20.2 g. (0.1 mole) bromoacetyl bromide. The mixture is cooled to about 5° C. Pyridine is added dropwise and the temperature is maintained between 5°–10° C. Upon completion of the addition, the reaction mixture is allowed to come to room temperature. At room temperature the solution clarifies. Stirring is continued for 1–2 hours to insure total reaction. The solution is washed successively with water, slightly acid wash (HCl) and water. After drying the organic layer over anhydrous magnesium sulfate, the solvent is evaporated. The obtained solid is washed with pentane. There is obtained 19.1 g. of the title compound, m.p. 96°–98° C.

EXAMPLE V

Preparation of 2'-acetoxy bromoacetanilide

In a similar manner as Example III, 6.9 g. of 3'-hydroxy bromoacetanlide was reacted with 2.8 g. acetyl chloride in 120 ml. of chloroform as solvent. Triethylamine, 3.6 g., was used as the base. The resulting product was washed with water, twice with sodium bicarbonate solution and twice with water. After drying over anhydrous magnesium sulfate and evaporating the solvent, there is obtained 9.0 g. of the title compound, m.p. 79°–82° C.

TABLE I

| Compound Number | $R_1$ | $R_2$ | Position | m.p. °C. or $n_D^{20}$ |
|---|---|---|---|---|
| 1 | H | H | meta | 167–170 |
| 2 | H | C(O)NHCH$_3$ | meta | 136–138 |
| 3 | H | C(O)NHCH(CH$_3$)$_2$ | meta | 144–149 |
| 4 | H | C(O)NHCH$_2$CH=CH$_2$ | meta | 122–125 |
| 5 | H | C(O)NH(cyclohexyl) | meta | 163–165 |
| 6 | H | H | para | 141–144 |
| 7 | H | C(O)CH$_2$Br | meta | 96–98 |
| 8 | H | C(O)CH$_2$CH$_3$ | meta | 85–88 |
| 9 | H | C(O)-(p-CH$_3$-phenyl) | meta | 165–168 |
| 10 | H | C(O)cyclohexyl | meta | 111–113 |
| 11 | H | C(O)CH$_3$ | meta | 79–82 |

Other examples of compounds falling within the generic formula presented herein, which are preparable by the aforedescribed procedures and which may be formulated into microbiocidal compositions and applied as herein illustrated, are:

| Compound Number | $R_1$ | $R_2$ | Position |
|---|---|---|---|
| 12 | C$_2$H$_5$ | H | meta |
| 13 | H | C(O)NH$_2$ | meta |
| 14 | CH$_3$ | C(O)NHCH$_3$ | meta |
| 15 | H | C(O)N(CH$_3$)$_2$ | meta |
| 16 | H | C(O)NH-n-C$_4$H$_9$ | meta |
| 17 | H | C(O)N(n-C$_4$H$_9$)$_2$ | meta |
| 18 | C$_2$H$_5$ | C(O)NH$_2$ | meta |
| 19 | C$_2$H$_5$ | C(O)NHCH$_3$ | meta |
| 20 | C$_2$H$_5$ | C(O)N(CH$_3$)$_2$ | meta |
| 21 | C$_2$H$_5$ | C(O)N(n-C$_4$H$_9$)$_2$ | meta |
| 22 | CH$_3$ | C(O)N(CH$_2$CH=CH$_2$)$_2$ | meta |
| 23 | CH$_3$ | C(O)N—(CH$_2$)$_6$ | meta |
| 24 | H | C(O)NH(phenyl) | meta |
| 25 | C$_2$H$_5$ | C(O)NH(phenyl) | meta |
| 26 | H | C(O)NH(CH$_2$CH$_2$OCH$_3$) | meta |
| 27 | C$_2$H$_5$ | C(O)NH(CH$_2$CH$_2$OC$_2$H$_5$) | meta |
| 28 | H | C(O)NH(benzyl) | meta |
| 29 | C$_2$H$_5$ | C(O)NH(benzyl) | meta |
| 30 | H | C(O)NH(CH$_2$CCl=CH$_2$) | meta |
| 31 | C$_2$H$_5$ | C(O)NH(CH$_2$CCl=CH$_2$) | meta |
| 32 | H | C(O)NH(p-NO$_2$-phenyl) | meta |
| 33 | C$_2$H$_5$ | C(O)NH(p-NO$_2$-phenyl) | meta |
| 34 | H | C(O)NH(p-Cl-phenyl) | meta |
| 35 | C$_2$H$_5$ | C(O)NH(m-Cl-phenyl) | meta |
| 36 | H | C(O)N(piperidinyl-CH$_3$) | meta |
| 37 | C$_2$H$_5$ | C(O)N(piperidinyl-CH$_3$) | meta |
| 38 | H | S(O$_2$)CH$_3$ | para |
| 39 | C$_2$H$_5$ | S(O$_2$)C$_2$H$_5$ | meta |
| 40 | H | C(O)OCH$_3$ | meta |
| 41 | H | C(O)OCH$_3$ | para |
| 42 | C$_2$H$_5$ | C(O)OCH$_3$ | para |
| 43 | C$_2$H$_5$ | C(O)OCH$_3$ | meta |
| 44 | C$_2$H$_5$ | C(O)OC$_2$H$_5$ | para |
| 45 | H | C(O)OC$_2$H$_5$ | meta |
| 46 | H | C(O)H | meta |
| 47 | H | C(O)H | para |
| 48 | C$_2$H$_5$ | C(O)H | meta |
| 49 | C$_2$H$_5$ | C(O)H | para |
| 50 | C$_2$H$_5$ | C(O)C$_2$H$_5$ | meta |
| 51 | C$_2$H$_5$ | C(O)CH$_3$ | para |
| 52 | C$_2$H$_5$ | S(O$_2$)phenyl | meta |
| 53 | H | S(O$_2$)(p-Cl-phenyl) | meta |
| 54 | C$_2$H$_5$ | S(O$_2$)(m-Cl-phenyl) | para |
| 55 | H | S(O$_2$)(m-NO$_2$-phenyl) | meta |
| 56 | H | S(O$_2$)(CH$_3$-phenyl) | meta |
| 57 | H | S(O$_2$)(p-CH$_3$O-phenyl) | meta |
| 58 | i-C$_3$H$_7$ | S(O$_2$)(p-CN-phenyl) | meta |
| 59 | H | S(O$_2$)(p-Br-phenyl) | meta |
| 60 | H | C(O)O-phenyl | meta |
| 61 | i-C$_3$H$_7$ | C(O)O(p-Cl-phenyl) | para |
| 62 | H | C(O)O(m-NO$_2$-phenyl) | meta |
| 63 | CH$_3$ | C(O)O(p-CH$_3$-phenyl) | meta |
| 64 | H | C(O)O(p-CH$_3$O-phenyl) | meta |
| 65 | CH$_3$ | C(O)O(o-CH$_3$-phenyl) | para |
| 66 | C$_2$H$_5$ | C(O)O(p-CN-phenyl) | meta |
| 67 | CH$_3$ | C(O)CH$_2$CH$_2$Cl | meta |
| 68 | H | C(O)-p-Cl-phenyl | para |
| 69 | CH$_3$ | C(O)-m-NO$_2$-phenyl | meta |
| 70 | C$_2$H$_5$ | C(O)-p-CH$_3$-phenyl | para |
| 71 | H | C(O)-p-CH$_3$O-phenyl | para |
| 72 | CH$_3$ | C(O)p-CN-phenyl | meta |
| 73 | H | C(O)-phenyl | meta |
| 74 | C$_2$H$_5$ | C(O)-phenyl | meta |
| 75 | C$_2$H$_5$ | C(O)NH(cyclohexyl) | para |
| 76 | H | C(O)NH(p-CN-phenyl) | meta |
| 77 | n-C$_4$H$_9$ | C(O)NH(p-CN-phenyl) | meta |
| 78 | H | C(O)NH(p-CH$_3$O-phenyl) | para |
| 79 | H | C(O)NH(p-CH$_3$O-phenyl) | meta |

| Compound Number | R₁ | R₂ | Position |
|---|---|---|---|
| 80 | CH₃ | C(O)NH(o-CH₃-phenyl) | meta |

As previously mentioned, the herein described compounds are microbiostatic agents which are useful and valuable in controlling fungi and bacteria. The compounds of this invention are tested as microbiocides in the following manner.

In Vitro Vial Tests. The compounds are tested to determine the microbiostatic efficacy when in contact with growing fungi or bacteria in an artificial medium. For each candidate compound, four 1-ounce vials are partially filled, two with malt broth and two with nutrient broth. The compound to be tested is placed in the vials at the desired concentration (expressed in parts per million). The vials containing malt broth are inoculated with water suspensions of spores of the desired fungi, *Aspergillus niger* and *Penicillium italicum*, and cells of the bacteria, *Escherichia coli* and *Staphylococcus aureus*, are inoculated into the vials containing nutrient broth (one specie of organism per vial). The vials are then sealed and held for one week, after which time the growth of the organisms is observed and noted. The tests are repeated using lower concentrations of the candidate compounds to determine the lowest concentration that can be used and still offer some control of the growth of the organism. Table II shows the results of the in Vitro tests.

TABLE II

In Vitro Test
Lowest Effective Concentration (p.p.m.)

| COMPOUND NUMBER | Aspergillus niger | Penicillium italicum | Escherichia coli | Staphylococcus aureus |
|---|---|---|---|---|
| 1 | 100 | (25) | (10) | 10 |
| 2 | >50 | >50 | 50 | 50 |
| 3 | (100) | (25) | 25 | 10 |
| 4 | >50 | 50 | >50 | 50 |
| 5 | >50 | (50) | (50) | 50 |
| 6 | 50 | 50 | 25 | 25 |
| 7 | >50 | 10 | 25 | 5 |
| 8 | 50 | 10 | 50 | 5 |
| 9 | >50 | >50 | >50 | 10 |
| 10 | >50 | 5 | >50 | 5 |
| 11 | 50 | 10 | 50 | 1 |
| A | >500 | (500) | (250) | (250) |
| B | >500 | >500 | >500 | >500 |

( ) = Indicates partial control at this concentration.
A = Chloro/analog of Compound Number 1.
B = Chloro/analog of Compound Number 3.

Soap Plug Test. Samples of Compounds No. 1 and 3, and 3,4,4-trichlorocarbanilide (TCC) are incorporated at a level of 1% in sodium stearate using acetone with the slurry. The products are air dried and pressed in a metal tube to form a soap plug approximately 10 mm. in diameter and 2 mm. thick. These are placed on nutrient agar plates that have been streaked separately with *Escherichia coli* and *Staphylococcus aureaus* cells. The plates are incubated at 37° C. for 17 hours. The radius of the zone of biological inhibition around the soap plug is measured. The data from this test are as follows:

TABLE III

| | Soap Plug Test Zone of Biological Inhibition (mm) | |
|---|---|---|
| COMPOUND NUMBER | Escherichia coli | Staphylococcus aureus |
| 3 | 2 | 6–8 |
| 1 | 2 | 12–15 |
| TCC | 0 | 5 |
| Blank | 0 | 0 |

Detergent Formulation Test. Samples of Compounds No. 1 and 3 of 10–20 mg. are dissolved in 5 ml. of acetone and added to weighed amounts of a commercial laundry detergent identified as "Tide ®", a trademark owned by Proctor and Gamble (a mixture of lauryl sulfate and alkyl benzenesulfonate with tripolyphosphate as a binder), to give a concentration of 0.2% in the detergent. From these detergent samples, 1 g. is added to 500 ml. of 50° C. tap water. To this wash solution is added 25 g. of laundered white cotton duck and the mixture agitated by stirring for 10 minutes. The cloth samples are hand wrung and each sample twice rinsed with stirring for 10 minutes in 500 ml. of 50° C. tap water. Thereafter, the cloth samples are hand wrung and air dried. Samples (1" square approximately) of the treated cloth samples are placed on nutrient agar plates that have been separately streaked with *Staphylococcus aureus, Escherichia coli, Brevibacterium ammoniagenes,* and *Trichophyton mentagrophytes.*

The following controls are included in this test: A blank and a control containing a commercial laundry detergent identified as "Dreft ®", a trademark owned by Proctor and Gamble (active ingredients are sodium doderyl-benzene sulfonate, sodium perborate), which contains the biocide 3,3,4-trichlorocarbanilide (TCC). The plates are incubated at 37° C. for various lengths of time to provide growth for the organisms at which time the zone of biological inhibition around the cloth samples is measured. The radius of the zone of biological inhibition around the cloth samples are reported in the following Table IV.

TABLE IV

| | Detergent Formulation Test Zone of Biological Inhibition (mm) | | | |
|---|---|---|---|---|
| Sample | Escherichia coli | Staphylococcus aureus | Brevibacterium ammoniagenes | Trichophyton mentagrophytes |
| Blank | 0 | 0 | 0 | 0 |
| "Dreft" Control | 0 | trace | 1 | 0 |
| Compound No. 1 | 2 | 3 | 0 | 1 |
| Compound No. 3 | 0 | 1 | 2–3 | 0 |

What is claimed is:
1. A compound having the formula

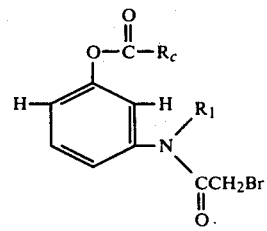

in which R_c is cyclohexyl and R₁ is hydrogen.

* * * * *